United States Patent
Brady

(10) Patent No.: US 7,303,582 B2
(45) Date of Patent: Dec. 4, 2007

(54) FOLDABLE ANGLE-FIXATED INTRAOCULAR LENS

(75) Inventor: Daniel Brady, San Juan Capistrano, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 24 days.

(21) Appl. No.: 10/394,906

(22) Filed: Mar. 21, 2003

(65) Prior Publication Data

US 2004/0186568 A1    Sep. 23, 2004

(51) Int. Cl.
*A61F 2/16* (2006.01)
(52) U.S. Cl. .................................. 623/6.43; 623/6.46
(58) Field of Classification Search .................. 623/6.6, 623/6.36–6.47, 6.51–6.52, 6.11–6.37
See application file for complete search history.

(56) References Cited

U.S. PATENT DOCUMENTS

| | | |
|---|---|---|
| 4,077,071 A | 3/1978 | Freeman |
| 4,093,361 A | 6/1978 | Erickson et al. |
| 4,134,160 A | 1/1979 | Bayers |
| 4,174,543 A | 11/1979 | Kelman |
| 4,249,272 A | 2/1981 | Polar |
| 4,254,509 A | 3/1981 | Tennant |
| 4,254,510 A | 3/1981 | Tennant |
| 4,316,293 A | 2/1982 | Bayers |
| 4,370,760 A | 2/1983 | Kelman |
| 4,377,873 A | 3/1983 | Reichart, Jr. |
| 4,403,353 A | 9/1983 | Tennant |
| 4,404,694 A | 9/1983 | Kelman |
| 4,424,597 A | 1/1984 | Schlegel |
| 4,446,581 A | 5/1984 | Blake |
| 4,480,340 A | 11/1984 | Shepard |
| 4,551,864 A | 11/1985 | Akhavi |
| 4,556,998 A | 12/1985 | Siepser |
| 4,560,383 A | 12/1985 | Leiske |
| 4,575,374 A | 3/1986 | Anis |
| 4,605,409 A | 8/1986 | Kelman |

(Continued)

FOREIGN PATENT DOCUMENTS

FR    2745711    9/1997

(Continued)

OTHER PUBLICATIONS

Apple et al., "Anterior chamber lenses. Part 1: Complications and pathology and a review of designs", *J. Cat. Refrac. Surg.*, vol. 13, pp. 157-174, Mar. 1987. (Best available copy).

(Continued)

*Primary Examiner*—Suzette Gherbi

(57) ABSTRACT

A foldable intraocular lens (IOL) includes an optic and at least one fixation member for supporting the optic in the anterior chamber of an eye. The fixation member includes an intermediate portion that extends a first direction away from the optic, and a leg portion that intersects with an outer end of the intermediate portion and extends a second direction, different from the first direction, away from the outer end. The leg portion preferably includes a reduced width region near the intersection with the intermediate portion. The reduced width region acts essentially as a hinge allowing the leg portion to flex about the intermediate portion in responsive to compressive forces, while the intermediate portion and optic remain stable.

18 Claims, 3 Drawing Sheets

U.S. PATENT DOCUMENTS

| | | | |
|---|---|---|---|
| 4,605,411 A | 8/1986 | Fedorov et al. | |
| 4,629,460 A | 12/1986 | Dyer | |
| 4,629,462 A | 12/1986 | Feaster | |
| 4,676,791 A | 6/1987 | LeMaster et al. | |
| 4,676,792 A | 6/1987 | Praeger | |
| 4,681,102 A | 7/1987 | Bartell | |
| 4,687,484 A | 8/1987 | Kaplan | |
| 4,687,485 A | 8/1987 | Lim et al. | |
| RE32,525 E | 10/1987 | Pannu | |
| 4,725,277 A | 2/1988 | Bissonette | |
| 4,734,095 A | 3/1988 | Seipser | |
| 4,781,717 A | 11/1988 | Grendahl | |
| 4,787,904 A | 11/1988 | Severin et al. | |
| 4,834,748 A | 5/1989 | McDonald | |
| 4,834,750 A * | 5/1989 | Gupta | 623/6.58 |
| 4,863,539 A | 9/1989 | Lee et al. | |
| 5,019,097 A | 5/1991 | Knight et al. | |
| 5,047,052 A | 9/1991 | Dubroff | |
| 5,071,432 A | 12/1991 | Baikoff | |
| 5,078,742 A | 1/1992 | Dahan | |
| 5,133,749 A | 7/1992 | Nordan | |
| 5,147,395 A | 9/1992 | Willis | |
| 5,147,397 A | 9/1992 | Christ et al. | |
| 5,197,981 A | 3/1993 | Southard | |
| 5,201,763 A | 4/1993 | Brady et al. | |
| 5,203,790 A | 4/1993 | McDonald | |
| 5,225,858 A | 7/1993 | Portney | |
| 5,258,025 A | 11/1993 | Fedorov et al. | |
| 5,433,745 A | 7/1995 | Graham et al. | |
| 5,476,513 A | 12/1995 | Brady et al. | |
| 5,628,796 A | 5/1997 | Suzuki | |
| 5,716,403 A | 2/1998 | Tran et al. | |
| 5,928,282 A * | 7/1999 | Nigam | 623/6.43 |
| 6,015,435 A | 1/2000 | Valunin et al. | |
| 6,051,024 A | 4/2000 | Cumming | |
| 6,179,870 B1 | 1/2001 | Sourdille et al. | |
| 6,190,410 B1 * | 2/2001 | Lamielle et al. | 623/6.51 |
| 6,200,344 B1 * | 3/2001 | Lamielle et al. | 623/6.51 |
| 6,224,628 B1 * | 5/2001 | Callahan et al. | 623/6.4 |
| 6,228,115 B1 * | 5/2001 | Hoffmann et al. | 623/6.49 |
| 6,238,433 B1 | 5/2001 | Portney | |
| 6,261,321 B1 | 7/2001 | Kellan | |
| 6,409,763 B1 | 6/2002 | Brady | |
| 6,475,240 B1 | 11/2002 | Paul | |
| 6,478,821 B1 | 11/2002 | Laguette et al. | |
| 6,482,229 B1 | 11/2002 | Gwon et al. | |
| 6,616,693 B1 * | 9/2003 | Nguyen | 623/6.43 |
| 6,723,124 B2 | 4/2004 | Brady | |
| 2003/0045933 A1 | 3/2003 | Brady | |
| 2004/0249456 A1 * | 12/2004 | Cumming | 623/6.37 |

FOREIGN PATENT DOCUMENTS

| | | |
|---|---|---|
| WO | 98/56315 | 12/1998 |

OTHER PUBLICATIONS

Marinho, A., "Results are encouraging for phakic IOLs, but more work is needed", *Ocular Surgery News*, Refractive Surgery, pp. 12-15, Feb. 15, 2000.

Baikoff et al., "Angle-fixated Anterior Chamber Phakic Intraocular Lens for Myopia of −7 to −19 Diopters", *J. Refrac. Surg.*, vol. 14, pp. 282-293, May/Jun. 1998.

Aliò et al., "Phakic Anterior Chamber Lenses for the Correction of Myopia", *Ophthalmology*, vol. 106, No. 3, pp. 458-466, Mar. 1999.

Apple et al., "Intraocular Lenses—Evolution, Designs, Complications, and Pathology", pp. 23-36 and pp. 205-221, Williams & Wilkins Copyright® 1989.

* cited by examiner

FOLDABLE ANGLE-FIXATED INTRAOCULAR LENS

This invention relates to intraocular lenses (IOLs). More particularly, the invention relates to IOLs placed in the anterior chambers of eyes which provide at least one benefit, for example, at least one of the following benefits: a reduction in the incidence of one or more complications in the eye caused by prior anterior chamber IOLs; effective foldability for safe and controlled insertion in the eye through a small incision; reduced IOL retention forces and a reduction in the tendency of the optics of the IOLs to vault due to a desirable compressive bias of the IOL when fit within the eye.

The human eye is susceptible to numerous disorders and diseases, a number of which attack the crystalline lens. For example, cataracts mar vision through cloudy or opaque discoloration of the lens of the eye, and can result in partial or complete blindness. When this happens, the crystalline lens can be removed and replaced with an intraocular lens, or IOL. In certain other circumstances, an IOL can be placed in an eye containing the natural crystalline lens, for example, to provide for enhanced vision in the phakic eye.

A typical IOL comprises an optic body, or lens, adapted to focus light toward the retina of the eye, and one or more fixation members, or haptics, adapted to at least assist in supporting or fixating the IOL in a suitable location in the eye, such as the anterior chamber, iris, or capsular bag of the eye. The design of the fixation members is to a large part dictated by the location in the eye in which the IOL is to be implanted. In general, conditions in the anterior chamber are more exacting than in the posterior chamber, since the ocular structures in and around the anterior chamber are subject to distortion, for instance, when a patient squints, rubs, or touches his or her eyelids, engages in rigorous physical activity, or receives an unexpected jolt or impact to the body, particularly the face. As a result, it is desirable that anterior chamber IOLs be provided with relatively flexible fixation members that yield readily when ocular distortion occurs, in order to minimize irritation or trauma to the eye. At the same time, the fixation members must not yield so readily as to result in decentration of the IOL and distortion of the visual image. In addition, the fixation members should provide sufficient axial stability to prevent the optic from vaulting forwardly (and potentially contacting the cornea) in response to compressive forces on the outer edges of the IOL.

Another factor to be taken into consideration in the design of anterior chamber IOLs is material. Typically, IOLs are classified as being either "hard" (i.e. rigid) or "soft" (i.e. flexible). In many cases, "soft" or "deformable" IOLs are preferred, since they can be rolled, folded, or otherwise deformed for insertion through a small or very small (e.g. less than 3.5 mm) incision in the eye. Small or very small incisions are generally desirable since they result in less surgical trauma and require a shorter recovery period than large incisions. Typical "soft" IOL materials include silicone polymeric materials, cross-linked acrylic polymeric materials, hydrophilic hydrogel materials, and the like. One disadvantage of many of these materials, however, is that they are relatively sticky. As a result, in some prior art foldable IOL designs, there has been a problem with the fixation members becoming stuck to the optic during insertion.

Other problems can occur if the IOL is not properly ejected from the insertion device. For instance, improperly designed fixation members can cause the IOL to twist or spin as it is ejected from the inserter, resulting in improper placement in, and possible damage to, the eye. Well-designed fixation members, on the other hand, should deploy in a suitable, e.g. planar, fashion as the IOL is ejected, allowing the IOL to be positioned as safely and accurately as possible.

Accordingly, it would be advantageous to provide anterior chamber IOLs which are effectively and safely foldable or deformable for insertion in the eye, fit a range of sizes of eyes, can be deployed from an inserter in a controlled, predictable manner, stabilize the optic from unwanted movement, minimize translational movement of the optic of the IOL along the optical axis, and otherwise reduce the known complications caused by prior art anterior chamber IOLs.

SUMMARY OF THE INVENTION

New IOLs for implantation in eyes, for example in anterior chambers of eyes, have been discovered. The present IOLs are sized and structured to be effectively fixated against the iridiocorneal angle of the anterior chamber while being substantially compatible with this delicate region of the eye. The present IOLs are foldable or deformable for insertion through a small incision in the eye. In particular, the IOLs of the present invention are designed and structured to be folded or deformed and inserted effectively and safely. The fixation members of the present IOLs preferably are structured to deploy in a substantially controlled, and preferably planar, manner when the IOL is ejected from an insertion device, which advantageously reduces the risk of the unfolding IOL causing damage to the eye.

Once positioned in the eye, the IOL is advantageously stabilized, exerts reduced retention forces, and/or the optic of the IOL has a substantially reduced tendency to vault anteriorly.

In accordance with one aspect of the present invention, an intraocular lens (IOL) comprises an optic and at least one fixation member for supporting the optic in the anterior chamber of an eye. The fixation member includes an intermediate portion that extends in a first direction from the peripheral edge of the optic, and at least one leg portion that intersects with an outer end of the intermediate portion and extends in a second direction away from the outer end. The at least one leg portion is configured to flex about a region of reduced width formed near the intersection of the intermediate portion and the leg portion. Advantageously, this intersection includes a curved inner edge.

In a preferred embodiment of the invention, the intermediate portion of the fixation member has a substantially uniform axial thickness, preferably equal to or less than the axial thickness of the peripheral edge of the optic. Preferably, the width of the intermediate portion is greater than the axial thickness of the intermediate portion. The at least one leg portion has a proximal portion including the region of reduced width, and a terminal portion configured to be received in the iridiocorneal angle of the eye. Advantageously, the proximal portion has a substantially uniform first axial thickness equal to or less than the axial thickness of the intermediate portion, and the terminal portion has a second axial thickness less than the first axial thickness.

The IOL is preferably symmetrical about a fold line, and the reduced width region of the at least one leg portion preferably has a width in a direction parallel to the fold line that is less than the first axial thickness.

Advantageously, the IOL includes two diametrically opposed fixation members, wherein each fixation member includes a pair of legs extending in opposite directions with respect to the fold line. A terminal portion of each leg has a distalmost point that is spaced from the distalmost point of the other leg by a distance greater than the diameter of the optic.

Preferably, the outer end of the intermediate portion includes a straight edge that extends generally perpendicular to the fold line and connects the two legs. This straight edge is advantageously at least about 1.5 mm long.

In accordance with a second aspect of the invention, a foldable IOL includes an optic having an optical axis and a peripheral edge, and at least one fixation member for supporting the optic in the anterior chamber of an eye. The at least one fixation member includes an intermediate portion that extends from the peripheral edge of the optic to a straight, or substantially straight, outer edge, and a pair of legs that intersect the intermediate region at the outer edge. The legs extend generally perpendicularly with respect to the intermediate region and in opposite directions with respect to one another. Preferably, each leg has a curved inner edge at the intersection between the leg and the intermediate portion.

Preferably, the IOL is symmetrical about a fold line, and the straight edge is perpendicular to the fold line. The straight edge is advantageously at least about 1.5 mm long.

Each leg preferably includes a proximal portion having a width in a direction parallel to the fold line. The width preferably has a minimum value near the intersection between the leg and the intermediate portion. Advantageously, the proximal portion has a substantially uniform first axial thickness that is greater than the minimum value of the width.

Each leg preferably also includes a terminal portion having a second axial thickness less than the first axial thickness. Advantageously, the terminal portion of each leg has a distalmost point spaced from the distalmost point of the terminal portion of the other leg by a distance greater than the diameter of the optic.

Preferably, the intermediate portion of each fixation member has a substantially uniform axial thickness greater than or equal to the first axial thickness and less than or equal to the axial thickness of the peripheral edge of the optic. Advantageously, the width of the intermediate portion is greater than the axial thickness of the intermediate portion throughout the length of the intermediate portion.

In accordance with a third aspect of the invention, a foldable IOL comprises an optic having optical axis and a peripheral edge, and at least one fixation member for supporting the optic in an anterior chamber of an eye. The fixation member includes an intermediate portion symmetrically disposed about a fold line extending through the optic, and at least one leg portion intersecting with an outer end of the intermediate portion. The at least one leg portion has a width in a direction parallel to the fold line, the width having a minimum value near the intersection between the leg and the intermediate portion.

Advantageously, the intermediate portion of the at least one fixation member has a uniform axial thickness that is preferably equal to or less than the axial thickness of the peripheral edge of the optic. Preferably, the width of the intermediate portion is greater than the axial thickness of the intermediate portion throughout the length of the intermediate portion.

In a preferred embodiment of the invention, the at least one leg portion comprises a pair of legs extending in opposite directions with respect to the fold line. Advantageously, each leg has a proximal portion having a first axial thickness that is equal to or less than the axial thickness of the intermediate portion of the fixation member and greater than the minimum value of the width of the leg portion. Each leg further includes a terminal portion configured to be received in an iridiocorneal angle of the eye. Preferably the terminal portion has a second axial thickness less than the first axial thickness.

Preferably, the terminal portion of each leg has a distalmost point that is spaced from the distalmost point of the terminal portion of the other leg by a distance greater than the diameter of the optic.

Advantageously, each leg includes a curved inner edge at the intersection with the intermediate portion.

Any and all of the features described herein and combinations of such features are included within the scope of the present invention provided that the features of any such combination are not mutually inconsistent.

These and other aspects and advantages of the present invention will become apparent in the following detailed description and claims, particularly when considered in conjunction with the accompanying drawings in which like parts bear like reference numerals.

DESCRIPTION OF THE PREFERRED EMBODIMENTS

Figure 1:
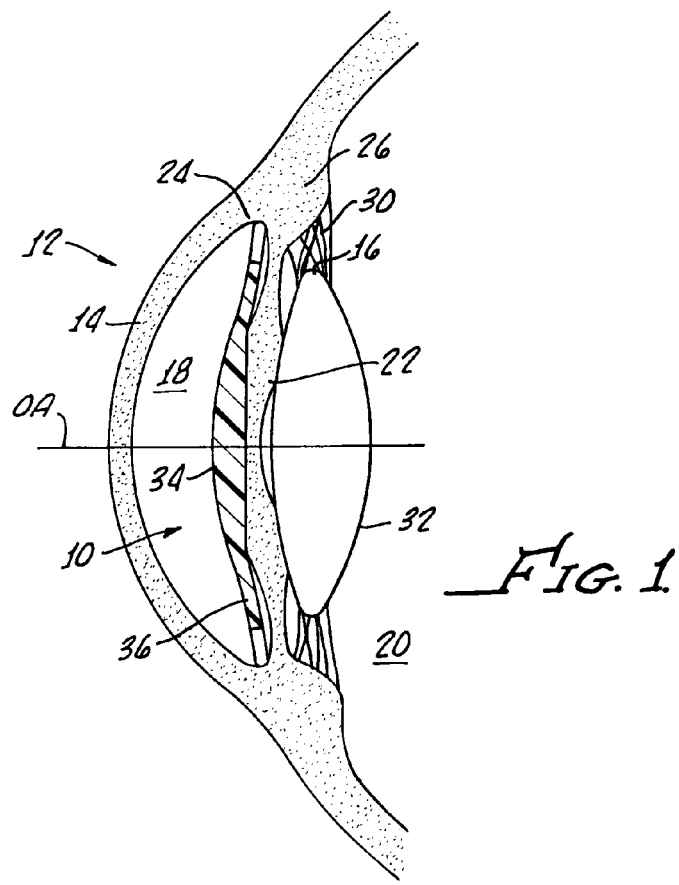
FIG. 1 is a cross-sectional view through a sagittal portion of a human eye, illustrating an IOL of the present invention mounted in the anterior chamber.

Referring now to FIG. 1, an anterior chamber IOL (IOL) 10 of the present invention is shown implanted in an eye 12. The eye 12 comprises a cornea 14 shown to the left or front of the eye and an annular iris 16 shown in the middle of the eye. The iris 16 divides the eye 12 into an anterior chamber 18 at the front of the eye and a posterior chamber 20 in back of the iris. The iris 16 also defines the aperture or pupil 22, which is a variable opening in the middle of the iris. The posterior face of the cornea 14 and the anterior face of the iris 16 meet at the scleral spur defining an iridiocorneal angle 24. Behind the iris 16 is the ciliary process 26, which controls the movements of the natural crystalline lens 32 of the eye 12 via a plurality of fibrous zonules 30.

Figure 2:
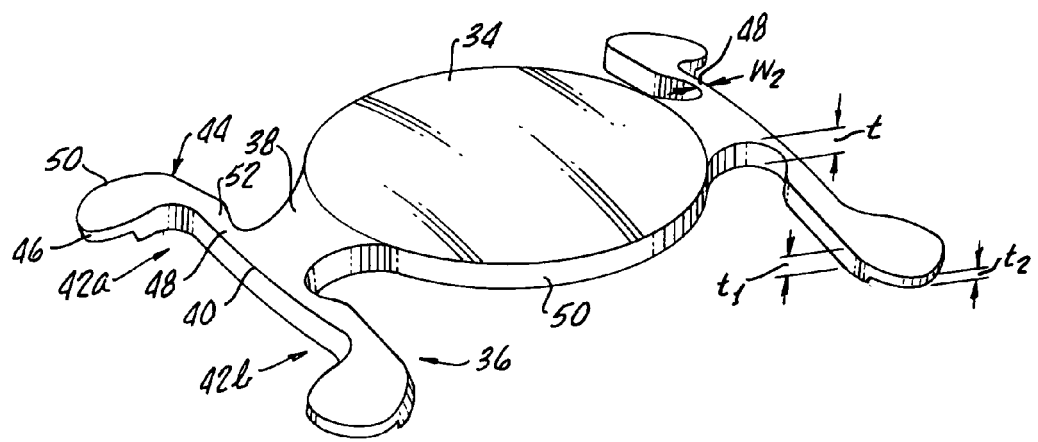
FIG. 2 is a perspective view of an anterior chamber IOL of the present invention.
Figure 3:
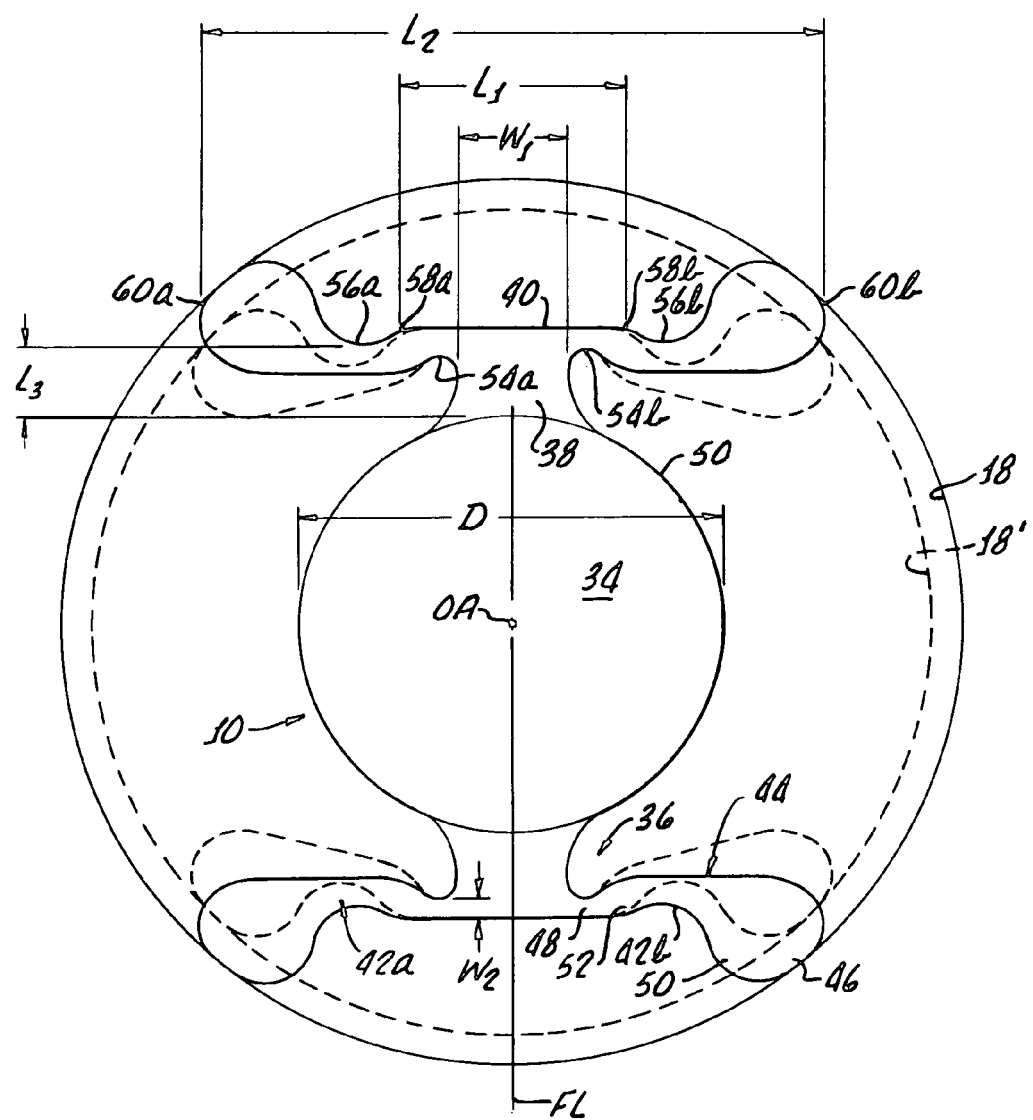
FIG. 3 is a frontal elevational view of the anterior chamber of the eye with the IOL of the present invention installed therein, showing preferred flexing of the IOL.
Figure 4:
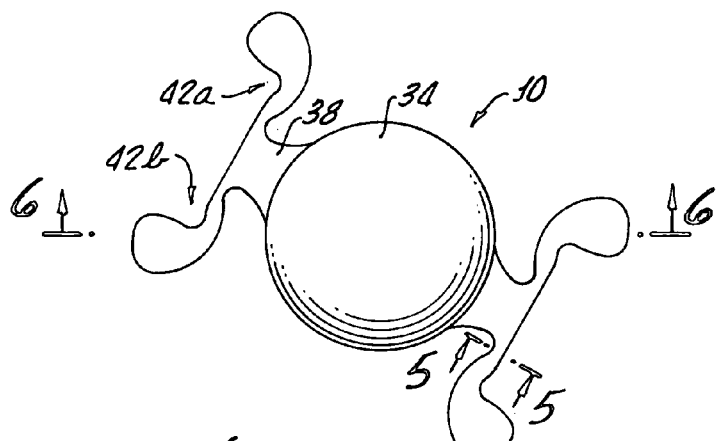
FIG. 4 is a frontal elevational view of the IOL of the present invention.
Figure 5:
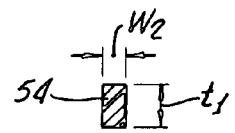
FIG. 5 is a sectional view taken through line 5-5 of FIG. 4.
Figure 6:
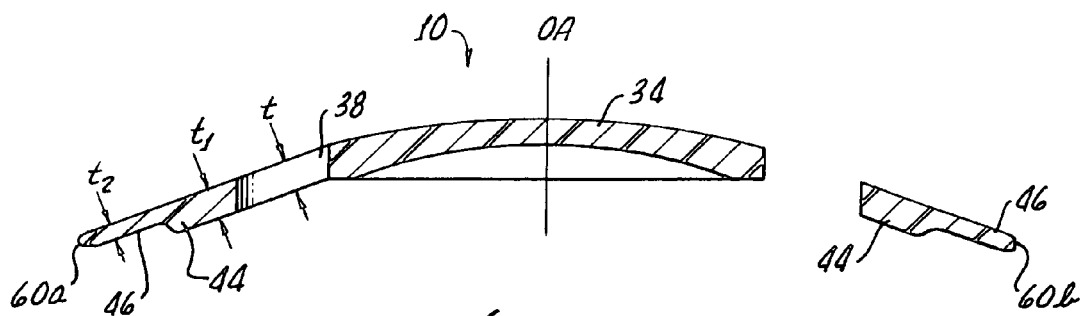
FIG. 6 is a sectional view taken through line 6-6 of FIG. 4.

Still referring to FIG. 1, with additional reference to FIGS. 2 and 3, the anterior chamber IOL 10 of the present invention comprises an optic 34 that is supported in front of the pupil 22 by fixation members 36, sometimes known as haptics. The fixation members 36 extend radially outwardly from the typically circular optic 34 to rest in and against or in contact with the iridiocorneal angle 24, and, as will be explained below, are designed to minimize retention forces and inhibit forward vaulting of the optic along the optical axis OA. The optical axis OA is an imaginary line that passes through the optical centers of both the anterior and posterior surfaces of the IOL 10, and in the human eye is generally aligned along the centers of the cornea 14, the natural lens 32 and the retina (not shown) of the eye 12. Desirably, the optical axis OA of the IOL 10 coincides with that of the natural eye.

When used as a refractive lens, the optic portion 34 of the IOL can be a positive powered lens from 0 to approximately +20 or more diopters, or a negative powered lens from 0 to approximately −25 or less diopters. The optic portion 34 can be biconvex, plano-convex, plano-concave, biconcave or concave-convex (meniscus), depending, for instance, upon the needs of the patient. In addition, the optic portion 34 may have a single optical power or may be multi-focal.

The IOLs of the present invention can be made from a variety of so-called soft biocompatible materials that can be folded, deformed, or compressed, such as silicone polymeric materials, acrylic polymeric materials, hydrogels, hydrogel-forming polymeric materials and mixtures thereof. The fixation members 36 may be formed separately from the optic portion 34 and connected through processes such as heat and/or physical staking and/or chemical bonding, or may be formed integrally with the optic portion 34 in a so-called single-piece IOL. In a preferred embodiment, an IOL of the present invention is made of a material, such as a cross-linked acrylic polymeric material, that can be folded for insertion through a small incision (e.g., less than 3.5 mm), and is desirably of one-piece construction.

The optic 34 of the IOL, which is typically circular and symmetrical about a fold line FL, has a diameter D that is preferably in the range of about 5.5 to about 6.5 mm, depending on the size of the patient's eye, and a peripheral edge 50, the thickness of which depends on the patient's prescription and other factors.

Each fixation member 36 includes an intermediate portion, or plate, 38 that extends from a peripheral edge 50 of the optic 34 to a straight outer edge 40. A pair of legs 42a, b, intersect the intermediate portion 38 at the outer edge 40. The legs 42a, b extend in opposite directions to one another, generally perpendicular to the fold line FL.

The intermediate portion 38 of each fixation member 36 has a uniform, or substantially uniform, axial thickness t that is equal to or less than, but not substantially less than, the peripheral edge 50 of the optic 34. In addition, the intermediate portion 38 has a width $w_1$ measured in a generally tangential direction (perpendicular to the fold line FL). Preferably, this width $w_1$ is substantially constant between the peripheral edge 50 of the optic 34 and the straight outer edge 40 of the intermediate portion 38, although it may decrease slightly in the distal direction. In addition, the width $w_1$ is greater than the axial thickness t throughout the length of the intermediate portion 38.

Each of the legs 42a and 42b includes a proximal portion 44 having a first, uniform or substantially uniform, axial thickness $t_1$, and a terminal portion 46 having a second, uniform or substantially uniform, axial thickness $t_2$. The thickness $t_1$ of the proximal portion 44 is advantageously equal to or less than, but not substantially less than, the thickness t of the intermediate portion 38, and greater than the thickness $t_2$ of the terminal portion 46.

The proximal portion 46 of each leg 42a, b includes a reduced width region 48 near the intermediate portion 38, and an enlarged pod region 50 near the terminal portion 46. The reduced width region 48 is joined to the pod region 50 by an elongated bridge region 52. The reduced width region 48 advantageously has a width $w_2$, measured in a generally radial direction (parallel to the fold line FL), that is less than the axial thickness $t_1$, at that point. The reduced width region 48 of each leg 42a, b acts essentially as a hinge or pivot point allowing that leg 42a, b to flex about the intermediate portion 38 in response to compressive forces, while the intermediate portion 38 and optic 34 remain substantially stationary.

Each leg 42a, b of each fixation member 36 includes an inner edge 54a, b, that curves inwardly at its intersection with intermediate portion 38 to form the reduced width region 48, and an outer edge 56a, b that merges at a proximal end 58a, b with the straight outer edge 40 of the intermediate region 38. The proximal ends 58a, b of adjacent legs 42a, b are separated by the length $L_1$ of the straight outer edge 40, which advantageously is at least about 1.5 mm long.

The terminal portion 46 of each leg 42a, b is curved to substantially match the contour of the iridiocorneal angle 24 of the eye 12 so that it can be comfortably received therein. Each terminal portion 46 includes a distalmost point 60a, b which is spaced from the distalmost point of the terminal portion of the adjacent leg 42a, b by a distance $L_2$ that is longer than the diameter D of the optic 34.

The solid lines in FIG. 3 show the IOL 10 as it would appear in a relaxed state within an identically sized anterior chamber 18. Although the IOL 10 fits closely within this chamber 18, there is no compression, and thus the IOL may tend to slide or otherwise move from its central position. The dashed lines show the IOL in a compressed configuration in an actual size anterior chamber 18', wherein the walls of the chamber 18' exert compressive forces against each of the terminal regions or pods 44, causing the legs 42a, b to flex or pivot inwardly about the reduced width region 48. At the same time, the intermediate region 38 and the optic 34 remain stable and relatively unaffected by the compression imparted by the surrounding eye. As a result, the optic 34 undergoes little radial compression, and remains substantially in place and centered along the optical axis OA.

The dimensions of the various elements of the IOL 10 relative to one another are selected to achieve maximum stability of the IOL 10 within the anterior chamber 18' of the eye 12. More specifically, the geometry and relative dimensions of the various elements are selected such that compressive forces exerted on the legs 42a, b will cause the legs 42a to flex about the intermediate region 38, while the intermediate region 38 and the optic 34 will tend to remain stationary.

In addition, the geometry and relative dimensions of the various elements minimize the potential for problems during release of the IOL from an insertion apparatus. For instance, the relatively large distance $L_2$ between the terminal regions 46 of adjacent legs 42a, b reduces the possibility of the terminal regions 46 coming into contact with, and sticking to, either the optic 34 or the rod of an insertion device (not shown). In addition, the straight edge 40 of the intermediate portion 38 provides an elongated flat surface for the insertion rod to contact. The legs 42a, b of the fixation members fold along either side of the rod, but make little or no actual contact with the rod because of the spacing provided by the edge 40. Also, because the legs 42a, b extend substantially parallel to a diameter of the optic 34 and are not significantly angled in a distal or proximal direction, the fixation members 42a, b tend to deploy in a planar fashion, with a minimum anterior/posterior profile. Because of this minimum profile, the IOL can be manipulated relatively safely within the limited space available in the phakic anterior chamber, with reduced risk of contacting and damaging the natural crystalline lens and/or the endothelium lining.

The IOL 10 can be effectively inserted into an anterior chamber of an eye and used to provide vision correction, for example, vision enhancement. In a typical situation, an anterior chamber IOL 10 according to the present invention may be placed in the load chamber of an IOL insertion cartridge (not shown) having folding leaves and a hollow distal tip. The leaves of the cartridge are moved from their open position to their closed position, bringing both the optic and fixation members into a folded or rolled configuration. The cartridge is then placed in a suitable insertion apparatus such that the distal tip of the cartridge projects through an distal opening in the insertion apparatus. The distal tip of the cartridge is then placed in or near a very small incision in the sclera or cornea of an eye 12, and a plunger or the like is advanced through the insertion apparatus, causing the IOL 10 to be passed through the outlet of the distal tip into the anterior chamber 18 of the eye. Once placed in the anterior chamber 10, the IOL may, if necessary, be repositioned using a needle or the like to obtain optimum stability and centration.

While this invention has been described with respect to various specific examples and embodiments, it is to be understood that the invention is not limited thereto and that it can be variously practiced within the scope of the following claims.

The invention claimed is:

1. A foldable intraocular lens (IOL) for implantation in the anterior chamber of an eye, the IOL comprising:
   an optic having an optical axis, and a peripheral edge; and
   at least one fixation member for supporting the optic in the anterior chamber, the fixation member including:
      an intermediate portion extending in a first direction from the peripheral edge of the optic, the intermediate portion having a uniform axial thickness, and
      at least one leg portion intersecting with an outer end of the intermediate portion and extending in a second direction different from the first direction away from the outer end, the at least one leg portion having a region of reduced width near the intersection with the intermediate portion, wherein the leg portion is configured to flex about the region of reduced width in response to compressive forces exerted on the fixation member;
   wherein the at least one leg portion comprises a pair of legs extending in opposite directions from one another and generally perpendicular with respect to the intermediate portion;
   wherein each leg of the at least one leg portion has a curved inner edge at the intersection with the intermediate portion.

2. A foldable IOL according to claim 1, wherein the at least one leg portion comprises a proximal portion including the region of reduced width, and a terminal portion configured to be received in the iridiocorneal angle of the eye, wherein the proximal portion has a substantially uniform first axial thickness equal to or less than the axial thickness of the intermediate portion.

3. A foldable IOL according to claim 2, wherein the terminal portion has a second axial thickness less than the first, axial thickness.

4. A foldable IOL according to claim 2, wherein the at least one fixation member is symmetrical about a line extending through the optic, and wherein the reduced width region of the at least one leg portion has a width in a direction parallel to the line that is less than the first axial thickness.

5. A foldable IOL according to claim 1, wherein:
   the IOL is symmetrical about a line extending through the optic;
   the at least one leg portion comprises a pair of legs extending in generally opposite directions with respect to the line; and
   the outer end of the intermediate portion includes a straight edge joining the two legs, the straight edge extending generally perpendicular to the line.

6. A foldable IOL according to claim 5, wherein the straight edge has a length of at least about 1.5 mm.

7. A foldable IOL according to claim 1, wherein the intermediate portion has a length and a width, and wherein the width of the intermediate portion is greater than the axial thickness of the intermediate portion through the length of the intermediate portion.

8. A foldable IOL according to claim 1, wherein the at least one leg portion comprises a proximal portion having a uniform first axial thickness equal to or less than the axial thickness of the intermediate portion and a terminal portion configured to be received in the iridiocorneal angle of the eye having a second axial thickness less than the first axial thickness.

9. A foldable IOL according to claim 1, wherein the optic has a diameter, each leg of the at least one leg portion extends substantially parallel to a diameter and is not significantly angled in a distal direction or a proximal direction.

10. A foldable intraocular lens (IOL) for implantation in the anterior chamber of an eye, the IOL comprising:
    an optic having an optical axis, and a peripheral edge; and
    at least one fixation member for supporting the optic in the anterior chamber, the fixation member including:
       an intermediate portion symmetrically disposed about a line extending through the optic, the intermediate portion having a uniform axial thickness, and
       at least one leg portion intersecting with an outer end of the intermediate portion, the leg portion having a width in a direction parallel to the line, the width having a minimum value near the intersection between the leg and the intermediate portion;
    wherein the at least one leg portion comprises a pair of legs extending in opposite directions from one another and generally perpendicular with respect to the line;
    wherein the at least one leg portion has a first axial thickness near the intersection with the intermediate portion, and a second axial thickness at a terminal portion configured to contact an iridiocorneal angle of the eye;
    wherein the second axial thickness is less than the first axial thickness.

11. A foldable IOL according to claim 10, wherein the first axial thickness is less than or equal to the axial thickness of the intermediate region.

12. A foldable IOL according to claim 10, wherein the minimum value of the width is less than the first axial thickness.

13. A foldable intraocular lens (IOL) for implantation in the anterior chamber of an eye, the IOL comprising:
    an optic having an optical axis, and a peripheral edge; and
    at least one fixation member for supporting the optic in the anterior chamber, the fixation member including:
       an intermediate portion symmetrically disposed about a line extending through the optic, the intermediate portion having a uniform axial thickness, and
       at least one leg portion intersecting with an outer end of the intermediate portion, the leg portion having a width in a direction parallel to the line, the width having a minimum value near the intersection between the leg and the intermediate portion;

wherein the at least one leg portion comprises a pair of legs extending in opposite directions from one another and generally perpendicular with respect to the line;

wherein each leg of the at least one leg portion has a curved inner edge at the intersection with the intermediate portion.

14. A foldable IOL according to claim 13, wherein the peripheral edge of the optic has an axial thickness substantially equal to the axial thickness of the intermediate portion.

15. A foldable IOL according to claim 13, wherein the intermediate portion has a length and a width, and wherein the width of the intermediate portion is greater than the axial thickness of the intermediate portion throughout the length of the intermediate portion.

16. A foldable IOL according to claim 13, wherein the at least one leg portion comprises a proximal portion having a uniform first axial thickness equal to or less than the axial thickness of the intermediate portion and a terminal portion configured to be received in the iridiocorneal angle of the eye having a second, axial thickness less than the first axial thickness.

17. A foldable IOL according to claim 13, wherein the optic has a diameter, each leg of the at least one leg portion extends substantially parallel to a diameter and is not significantly angled in a distal direction or a proximal direction.

18. A foldable intraocular lens (IOL) for implantation in the anterior chamber of an eye, the IOL comprising:

an optic having an optical axis, and a peripheral edge; and at least one fixation member for supporting the optic in the anterior chamber, the fixation member including:

an intermediate portion extending in a first direction from the peripheral edge of the optic, the intermediate portion having a uniform axial thickness; and at least one leg portion intersecting with an outer end of the intermediate portion and extending in a second direction different from the first direction away from the outer end, the at least one leg portion having a region of reduced width near the intersection with the intermediate portion, wherein the leg portion is configured to flex about the region of reduced width in response to compressive forces exerted on the fixation member;

wherein the at least one leg portion has a terminal end, the terminal end having a thickness that is less than a thickness of the intermediate portion.

* * * * *